(12) United States Patent
Burbank et al.

(10) Patent No.: US 11,364,029 B2
(45) Date of Patent: Jun. 21, 2022

(54) STAPLER RELOAD DETECTION AND IDENTIFICATION

(71) Applicant: Intuitive Surgical Operations, Inc., Sunnyvale, CA (US)

(72) Inventors: William Burbank, Sunnyvale, CA (US); Matthew A. Wixey, Sunnyvale, CA (US); Nicholas Ragosta, Sunnyvale, CA (US); David W. Weir, Sunnyvale, CA (US); Emily Cooper, Sunnyvale, CA (US); Melody Wu, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 165 days.

(21) Appl. No.: 16/331,692

(22) PCT Filed: Sep. 8, 2017

(86) PCT No.: PCT/US2017/050747
§ 371 (c)(1),
(2) Date: Mar. 8, 2019

(87) PCT Pub. No.: WO2018/049206
PCT Pub. Date: Mar. 15, 2018

(65) Prior Publication Data
US 2019/0200989 A1     Jul. 4, 2019

Related U.S. Application Data

(60) Provisional application No. 62/385,649, filed on Sep. 9, 2016.

(51) Int. Cl.
*A61B 17/00* (2006.01)
*A61B 17/068* (2006.01)
(Continued)

(52) U.S. Cl.
CPC ........ *A61B 17/07207* (2013.01); *A61B 34/00* (2016.02); *A61B 34/30* (2016.02);
(Continued)

(58) Field of Classification Search
CPC .... A61B 17/07207; A61B 2017/07214; A61B 2017/07271; A61B 2017/07278; A61B 2017/00017; A61B 17/00
(Continued)

(56) References Cited

U.S. PATENT DOCUMENTS

2007/0175949 A1*  8/2007  Shelton, IV ........... A61B 34/76
                                                227/176.1
2010/0089970 A1   4/2010  Smith et al.
(Continued)

FOREIGN PATENT DOCUMENTS

CN    101224116 A    7/2008
CN    101686832 A    3/2010
(Continued)

OTHER PUBLICATIONS

International Search Report and Written Opinion for Application No. PCT/US2017/050747, dated Dec. 14, 2017, 9 pages.
(Continued)

*Primary Examiner* — Gloria R Weeks
(74) *Attorney, Agent, or Firm* — Artegis Law Group, LLP

(57) ABSTRACT

Surgical devices, systems, and related methods provide automated assessment of the status of a surgical instrument. A surgical device is configured to staple tissue via a replaceable stapler cartridge. The surgical device includes a pusher member configured to articulate the stapler cartridge to deploy staples. The surgical device includes an actuation mechanism that articulates the pusher member and a control unit configured to control operation of the actuation mechanism to attempt move the pusher member from a first
(Continued)

position to a second position subject to an output limit for the actuation mechanism and determine an attribute of the stapler cartridge based on an amount of movement of the pusher member achieved. The determined attribute can indicate a type of the stapler cartridge selected from different stapler cartridges, whether the stapler cartridge has already been fired, or that no stapler cartridge is mounted to the surgical device.

21 Claims, 11 Drawing Sheets

(51) Int. Cl.
*A61B 17/072* (2006.01)
*A61B 34/00* (2016.01)
*A61B 90/00* (2016.01)
*A61B 34/30* (2016.01)
*A61B 34/35* (2016.01)

(52) U.S. Cl.
CPC ..... *A61B 34/35* (2016.02); *A61B 2017/00017* (2013.01); *A61B 2017/0023* (2013.01); *A61B 2017/00075* (2013.01); *A61B 2017/07278* (2013.01); *A61B 2017/07285* (2013.01); *A61B 2090/0814* (2016.02)

(58) Field of Classification Search
USPC .................. 227/175.2, 175.3, 175.4, 182.1
See application file for complete search history.

(56) References Cited

U.S. PATENT DOCUMENTS

| | | | |
|---|---|---|---|
| 2010/0230465 A1 | 9/2010 | Smith et al. | |
| 2010/0294828 A1 | 11/2010 | Bindra et al. | |
| 2011/0022032 A1 | 1/2011 | Zemlok et al. | |
| 2011/0290856 A1* | 12/2011 | Shelton, IV | A61B 34/76 227/180.1 |
| 2011/0309128 A1* | 12/2011 | Okoniewski | A61B 17/068 227/176.1 |
| 2012/0248167 A1 | 10/2012 | Flanagan et al. | |
| 2013/0206814 A1 | 8/2013 | Morgan et al. | |
| 2013/0299556 A1 | 11/2013 | Marczyk et al. | |
| 2014/0175150 A1* | 6/2014 | Shelton, IV | A61B 17/07207 227/176.1 |
| 2014/0224856 A1* | 8/2014 | Smith | A61B 17/068 227/175.1 |
| 2015/0272575 A1* | 10/2015 | Leimbach | A61B 17/072 227/175.3 |
| 2015/0327862 A1 | 11/2015 | Kostrzewski et al. | |
| 2016/0058450 A1* | 3/2016 | Shelton, IV | A61B 17/07207 227/176.1 |
| 2016/0106429 A1 | 4/2016 | Burbank et al. | |
| 2016/0256160 A1 | 9/2016 | Shelton, IV et al. | |

FOREIGN PATENT DOCUMENTS

| | | |
|---|---|---|
| CN | 102048567 A | 5/2011 |
| CN | 103619269 A | 3/2014 |
| CN | 105682572 A | 6/2016 |
| CN | 105899148 A | 8/2016 |
| EP | 2789299 A1 | 10/2014 |
| EP | 2853222 A1 | 4/2015 |
| EP | 2878274 A1 | 6/2015 |
| EP | 2992836 A2 | 3/2016 |
| JP | 2011078773 A | 4/2011 |
| JP | 2011189136 A | 9/2011 |
| WO | WO-03094747 A1 | 11/2003 |
| WO | WO-2013063523 A1 | 5/2013 |
| WO | WO-2015109395 A1 | 7/2015 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP17849642.8 dated Mar. 3, 2020, 9 pages.

* cited by examiner

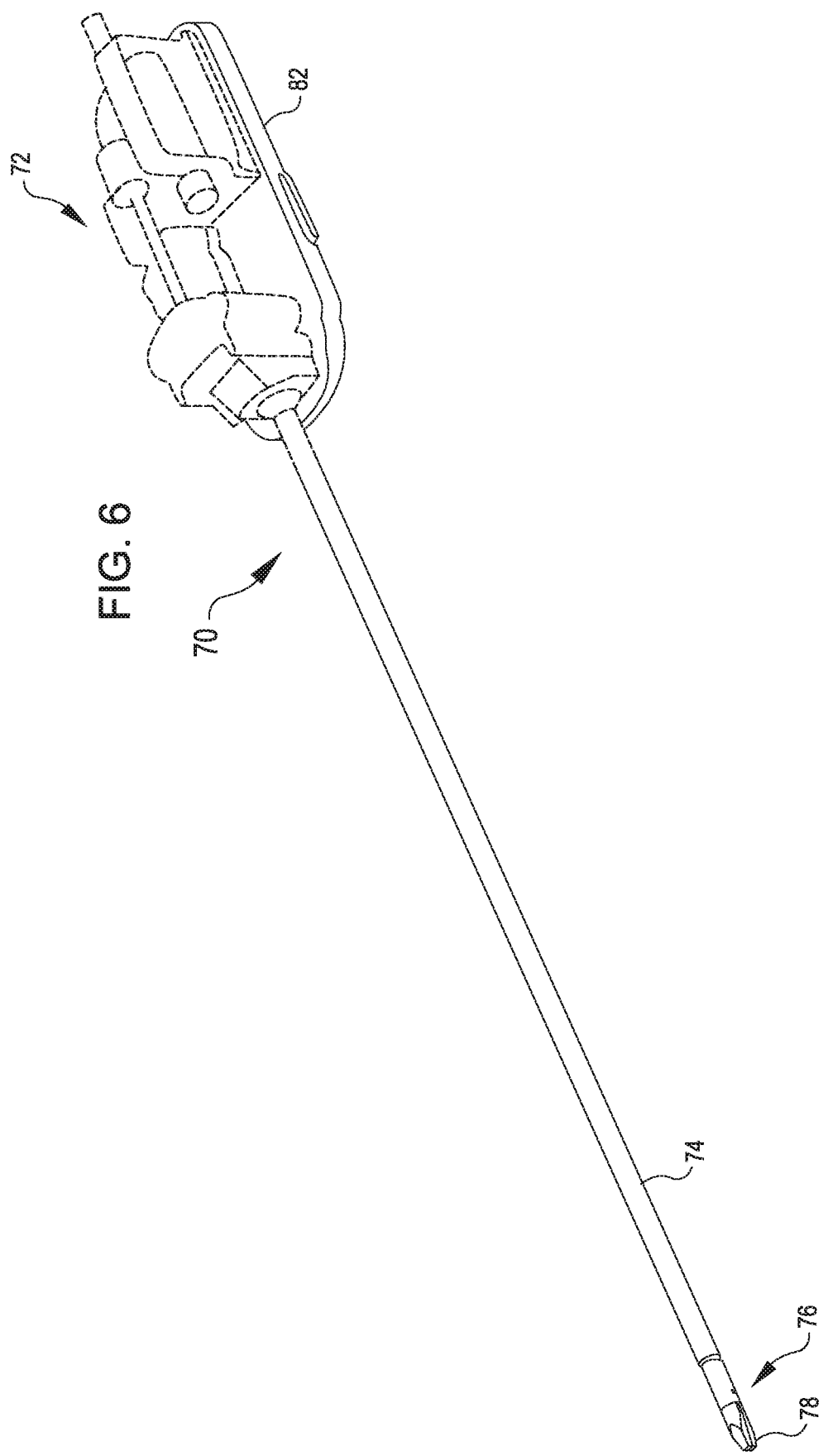

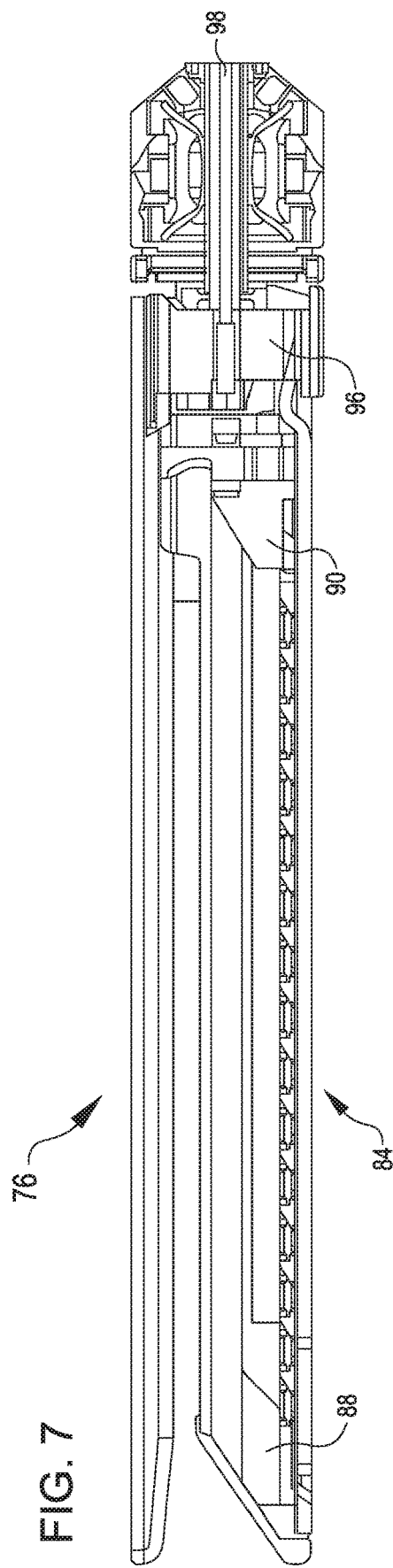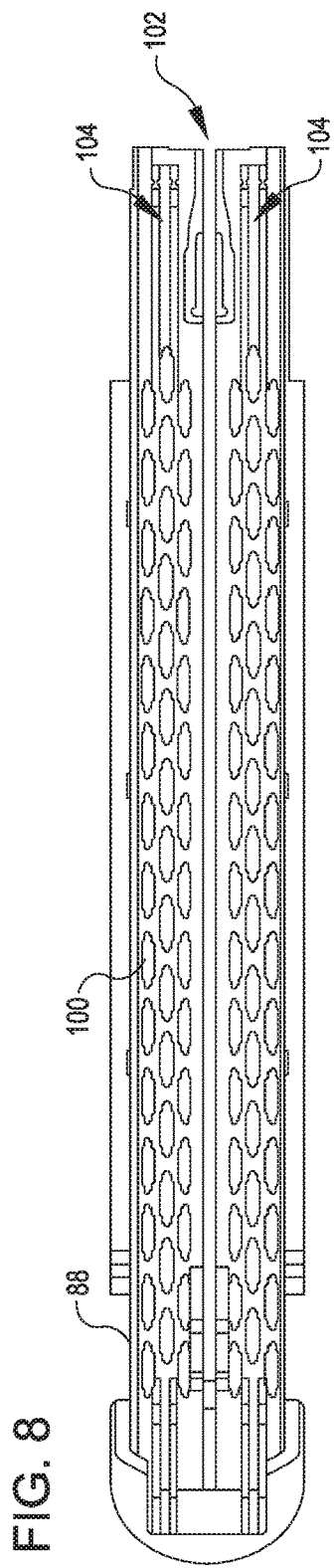

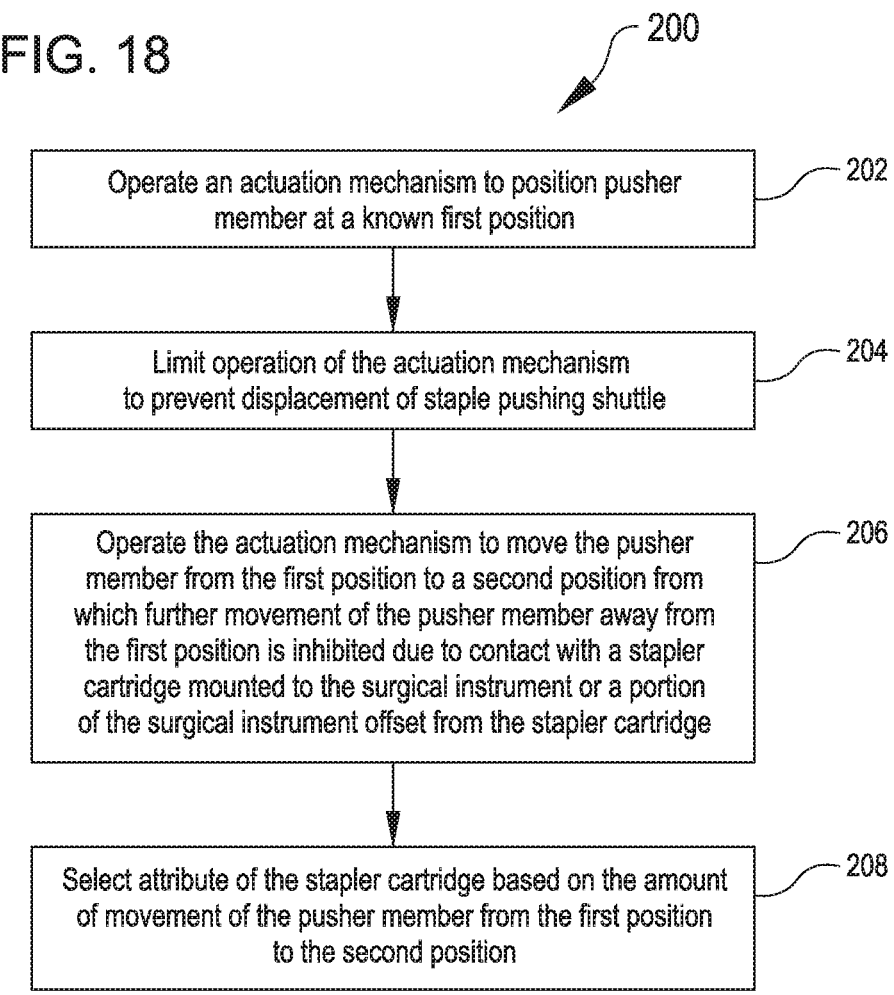

STAPLER RELOAD DETECTION AND IDENTIFICATION

CROSS REFERENCE TO RELATED APPLICATION DATA

The present application is a U.S. National Stage Application of PCT/US2017/050747 filed Sep. 8, 2017; which claims the benefit of U.S. Provisional Appln. No. 62/385,649 filed Sep. 9, 2016; the full disclosures which are incorporated herein by reference in their entirety for all purposes.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices.

Surgical clamping and cutting instruments (e.g., non-robotic linear clamping, stapling, and cutting devices, also known as surgical staplers; and electrosurgical vessel sealing devices) have been employed in many different surgical procedures. For example, a surgical stapler can be used to resect a cancerous or anomalous tissue from a gastro-intestinal tract. Many known surgical clamping and cutting devices, including known surgical staplers, have opposing jaws that clamp tissue and an articulated knife to cut the clamped tissue.

Many surgical clamping and cutting instruments include an instrument shaft supported end effector to which a replaceable stapler cartridge is mounted. An actuation mechanism articulates the stapler cartridge to deploy staples from the stapler cartridge to staple tissue clamped between the stapler cartridge and an articulable jaw of the end effector. Different types of stapler cartridges can be used that have different staple lengths suitable for different tissues to be stapled.

The use of replaceable stapler cartridges does, however, give rise to some additional issues. For example, prior to use, a suitable stapler cartridge having the correct staple length should be mounted to the end effector. If a stapler cartridge having an unsuitable staple length is mistakenly mounted to the end effector, the tissue may be stapled with the unsuitable length staples if the error is not detected and corrected prior to stapling of the tissue. As another example, if a previously used stapler cartridge is not replaced with a suitable new stapler cartridge, the tissue clamped between the previously used stapler cartridge and the articulable jaw cannot be stapled due to the lack of staples to deploy. A similar problem can arise if no stapler cartridge is mounted to the end effector.

Thus, there is believed to be a need for improved surgical systems configurable to staple tissue, surgical devices configured to staple tissue, and related methods that check whether a suitable stapler cartridge is mounted to a clamping and stapling surgical instrument prior to use. Preferably, the improved surgical systems, surgical devices, and related methods check whether a stapler cartridge is mounted to the surgical instrument, whether the mounted stapler cartridge is new or has already been fired, and the type of the mounted stapler cartridge to ensure that the mounted stapler cartridge has a suitable staple length for the tissue to be stapled.

BRIEF SUMMARY

Improved surgical systems configurable to staple tissue, surgical devices configured to staple tissue, and related methods are provided that check whether a suitable stapler cartridge is mounted to a surgical instrument prior to use. In many embodiments, the improved surgical systems, surgical devices, and related methods check whether a stapler cartridge is mounted, whether the stapler cartridge is new or has already been fired, and the type of the stapler cartridge to ensure that a stapler cartridge having a suitable staple length is mounted. By verifying that a suitable un-fired stapler cartridge is mounted to a surgical instrument prior to attempting to staple tissue with the surgical instrument, instances of improper tissue stapling may be reduced.

Thus, in one aspect, a method is provided for assessing operational status of a surgical instrument for stapling tissue via a replaceable stapler cartridge. The method includes operating, under the control of a control unit, an actuation mechanism drivingly coupled with a pusher member to attempt to move the pusher member from a first position to a second position subject to an output limit for the actuation mechanism. The movement of the pusher member is discontinued if the output limit for the actuation mechanism is exceeded during the attempt to move the pusher member from the first position to the second position. The control unit determines a parameter indicative of an amount of movement of the pusher member achieved during the attempt to move the pusher member from the first position to the second position. The control unit determines, based on the parameter, an operational status of the surgical instrument relating to the replaceable stapler cartridge.

In many embodiments, the method includes detecting if no replaceable stapler cartridge is mounted to the surgical instrument. For example, in response to the pusher member reaching the second position during the attempt to move the pusher member from the first position to the second position, the determination of the operational status by the control unit, based on the parameter, can include determining that no replaceable stapler cartridge is mounted to the surgical instrument.

In many embodiments, the method includes detecting if a replaceable stapler cartridge is mounted to the surgical instrument. For example, in response to the pusher member stopping movement at a stop position due to an exceedance of the output limit for the actuation mechanism during the attempt to move the pusher member from the first position to the second position, the determination of the operational status by the control unit, based on the parameter, can include determining that a replaceable stapler cartridge is mounted to the surgical instrument.

In many embodiments, the method includes detecting if a replaceable stapler cartridge mounted to the surgical instrument has already been fired. For example, in response to the pusher member stopping, due to an exceedance of the output limit for the actuation mechanism during the attempt to move the pusher member from the first position to the second position, at a stop position located within an initial range of motion between the first position and the second position, the determination of the operational status by the control unit, based on the parameter, can include determining that the replaceable stapler cartridge mounted to the surgical instrument has already been fired.

In many embodiments, the method includes detecting if the replaceable stapler cartridge mounted to the surgical instrument has not been fired. For example, in response to the pusher member stopping, due to an exceedance of the output limit for the actuation mechanism during the attempt to move the pusher member from the first position to the second position, at a stop position located outside an initial range of motion between the first position and the second position, the determination of the operational status by the control unit, based on the parameter, can include determining that the replaceable stapler cartridge mounted to the surgical instrument has not been fired.

In many embodiments, the method includes determining a type of a replaceable stapler cartridge mounted to the surgical instrument. For example, in response to the pusher member stopping, due to an exceedance of the output limit for the actuation mechanism during the attempt to move the pusher member from the first position to the second position, at a stop position located outside an initial range of motion between the first position and the second position, the determination of the operational status by the control unit, based on the parameter, can include determining a type of the replaceable stapler cartridge mounted to the surgical instrument from a plurality of types of the replaceable stapler cartridge.

In many embodiments, the method further includes operating the actuation mechanism to move the pusher member to a third position further away from the first position than the second position subject to a second output limit for the actuation mechanism greater than the output limit for the actuation mechanism. The movement of the pusher member can be discontinued if the second output limit for the actuation mechanism is exceeded during the attempt to move the pusher member to the third position.

The method can include operating the actuation mechanism, under the control of the control unit, to position the pusher member at the first position prior to the attempt to move the pusher member from the first position to the second position. For example, operating the actuation mechanism to position the pusher member at the first position prior to the attempt to move the pusher member from the first position to the second position can include moving the pusher member away from the second position into contact with a portion of the surgical instrument that blocks further movement of the pusher member away from the second position.

The method can include constraining a staple pushing shuttle of the replaceable stapler cartridge with a body of the replaceable stapler cartridge. Constraining the staple pushing shuttle with the body can be used to: (a) position the staple pushing shuttle relative to the body of the replaceable stapler cartridge; and/or (b) inhibit displacement of the staple pushing shuttle relative to the body of the replaceable stapler cartridge when the replaceable stapler cartridge is contacted by the pushing member during the attempt to move the pusher member from the first position to the second position.

In another aspect, a surgical system configurable to staple tissue via a replaceable stapler cartridge is provided. The surgical system includes an end effector, a pusher member, an elongated shaft, a proximal chassis, a manipulator, an actuation mechanism, and a control unit. The end effector is configured for mounting of a replaceable stapler cartridge to the end effector. A pusher member is configured to push a staple pushing shuttle included in the replaceable stapler cartridge to deploy staples from the replaceable stapler cartridge. The end effector is mounted at a distal end of the elongated shaft. The proximal chassis supports a proximal end of the elongated shaft and includes an actuation input drivingly coupled with the pusher member. The proximal chassis can be mounted to the manipulator. The manipulator includes an actuation output configured to be drivingly coupled with the actuation input. The actuation mechanism is drivingly coupled with the actuation output. The control unit is configured to: (a) control operation of the actuation mechanism to articulate the actuation output so as to attempt to move the pusher member from a first position to a second position subject to an output limit for the actuation mechanism, wherein movement of the pusher member is discontinued if the output limit for the actuation mechanism is exceeded; (b) determine a parameter indicative of an amount of movement of the pusher member achieved during the attempt to move the pusher member from the first position to the second position; and (c) determine, based on the parameter, an operational status of the surgical instrument relating to the replaceable stapler cartridge.

In many embodiments, the surgical system is configured to detect if no replaceable stapler cartridge is mounted to the surgical instrument. For example, the control unit can be configured to determine that no replaceable stapler cartridge is mounted to the surgical instrument in response to the pusher member reaching the second position during the attempt to move the pusher member from the first position to the second position.

In many embodiments, the surgical system is configured to detect if a replaceable stapler cartridge is mounted to the surgical instrument. For example, the control unit can be configured to determine that a replaceable stapler cartridge is mounted to the surgical instrument in response to the pusher member stopping at a stop position due to an exceedance of the output limit for the actuation mechanism during the attempt to move the pusher member from the first position to the second position.

In many embodiments, the surgical system is configured to detect if a replaceable stapler cartridge mounted to the surgical instrument has already been fired. For example, the control unit can be configured to determine that the replaceable stapler cartridge mounted to the surgical instrument has already been fired in response to the stop position being located within an initial range of motion between the first position and the second position.

In many embodiments, the surgical system is configured to detect if a replaceable stapler cartridge mounted to the surgical instrument has not been fired. For example, the control unit can be configured to determine that the replaceable stapler cartridge mounted to the surgical instrument has not been fired in response to the stop position being located outside an initial range of motion between the first position and the second position.

In many embodiments, the surgical system is configured to detect a type of a replaceable stapler cartridge mounted to the surgical instrument. For example, the control unit can be configured to determine, based on the parameter, a type of the replaceable stapler cartridge mounted to the surgical instrument from a plurality of types of the replaceable stapler cartridge.

In many embodiments of the surgical system, the actuation mechanism is operable subject to a second output limit for the actuation mechanism that is greater than the output limit for the actuation mechanism. For example, the control unit can be configured to operate the actuation mechanism to move the pusher member to a third position further away from the first position than the second position subject to a second output limit for the actuation mechanism greater than the output limit for the actuation mechanism, wherein movement of the pusher member is discontinued if the second output limit for the actuation mechanism is exceeded.

In many embodiments of the surgical system, the control unit is configured to operate the actuation mechanism to position the pusher member at the first position prior to the attempt to move the pusher member from the first position to the second position. For example, the control unit can be configured to operate the actuation mechanism to move the pusher member away from the second position into contact with a portion of the surgical instrument that blocks further movement of the pusher member away from the second position to position the pusher member at the first position.

In many embodiments of the surgical system, the replaceable stapler cartridge comprises a staple pushing shuttle and a body that constrains the staple pushing shuttle. For example, the staple pushing shuttle can be constrained via the body to: (a) position the staple pushing shuttle relative to the body of the replaceable stapler cartridge; and/or (b) inhibit displacement of the staple pushing shuttle relative to the body of the replaceable stapler cartridge when the replaceable stapler cartridge is contacted by the pushing member during the attempt to move the pusher member from the first position to the second position.

In another aspect, a surgical system configured to staple tissue via a replaceable stapler cartridge is provided. The surgical device includes an end effector, a pusher member, an actuation mechanism, and a control unit. The end effector is configured for mounting of a replaceable stapler cartridge to the end effector. The pusher member is configured to articulate the replaceable stapler cartridge to deploy staples from the replaceable stapler cartridge. The actuation mechanism is drivingly coupled with the pusher member. The control unit is configured to: (a) control operation of the actuation mechanism to attempt to move the pusher member from a first position to a second position subject to an output limit for the actuation mechanism, wherein movement of the pusher member is discontinued if the output limit for the actuation mechanism is exceeded; and (b) determine an attribute of the stapler cartridge based on an amount of movement of the pusher member achieved during the attempt to move the pusher member from the first position to the second position, the determined attribute of the stapler cartridge indicating: (1) a type of the replaceable stapler cartridge selected from a plurality of types of the replaceable stapler cartridges; (2) whether the replaceable stapler cartridge has already been fired; or (3) that no replaceable stapler cartridge is mounted to the end effector.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 6 is a perspective view of a robotic surgery tool that includes an end effector having opposed clamping jaws, in accordance with many embodiments.

FIG. 7 is a cross-sectional side view of an end effector of a surgical instrument with a mounted stapler cartridge, in accordance with many embodiments.

FIG. 8 is a top view of a body of a stapler cartridge of FIG. 7.

FIG. 18 is a simplified block diagram of acts of a method of assessing an operational status of a surgical instrument for stapling tissue, in accordance with many embodiments.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Minimally Invasive Robotic Surgery

Figure 1:
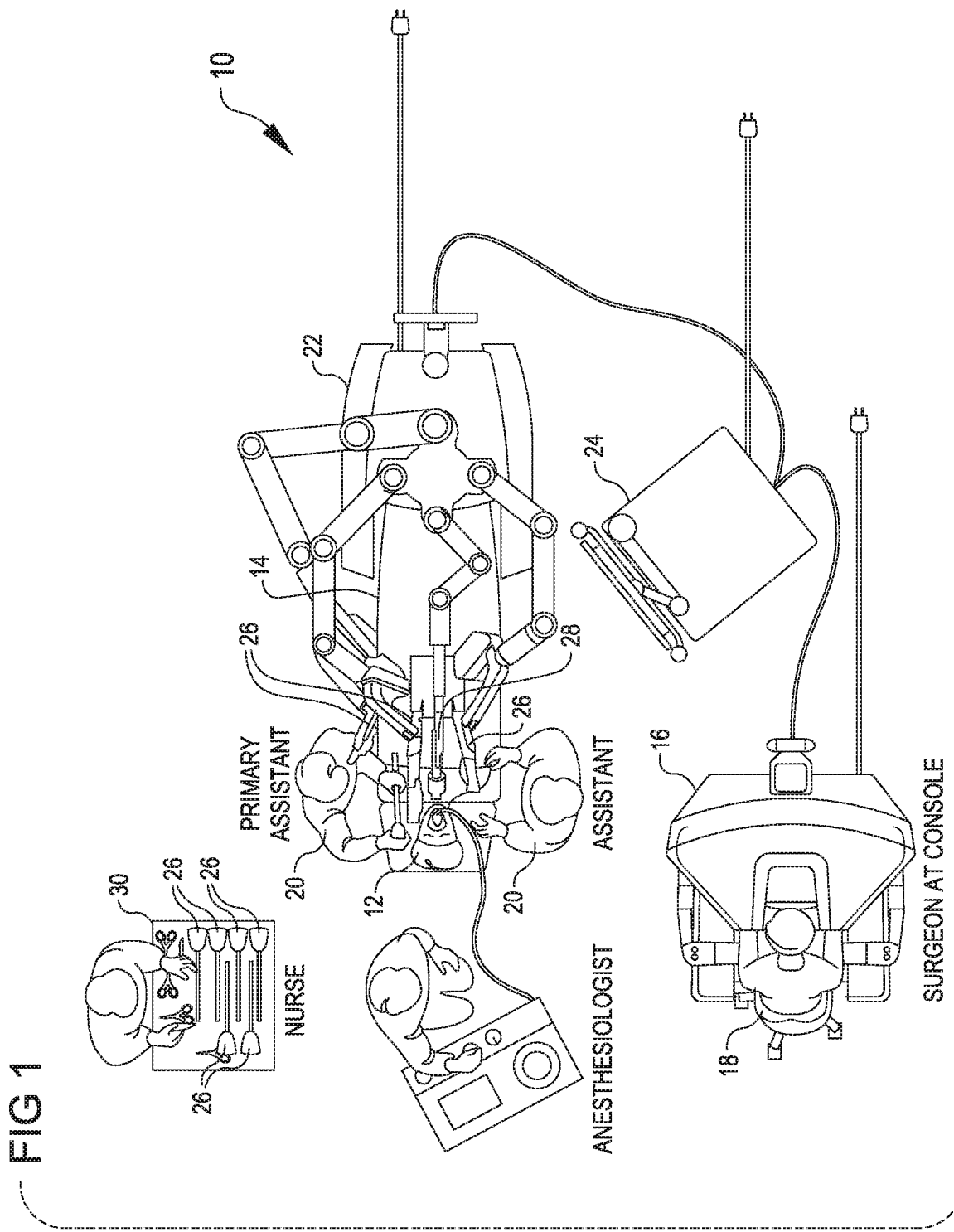
FIG. 1 is a plan view of a minimally invasive robotic surgery system being used to perform a surgery, in accordance with many embodiments.

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
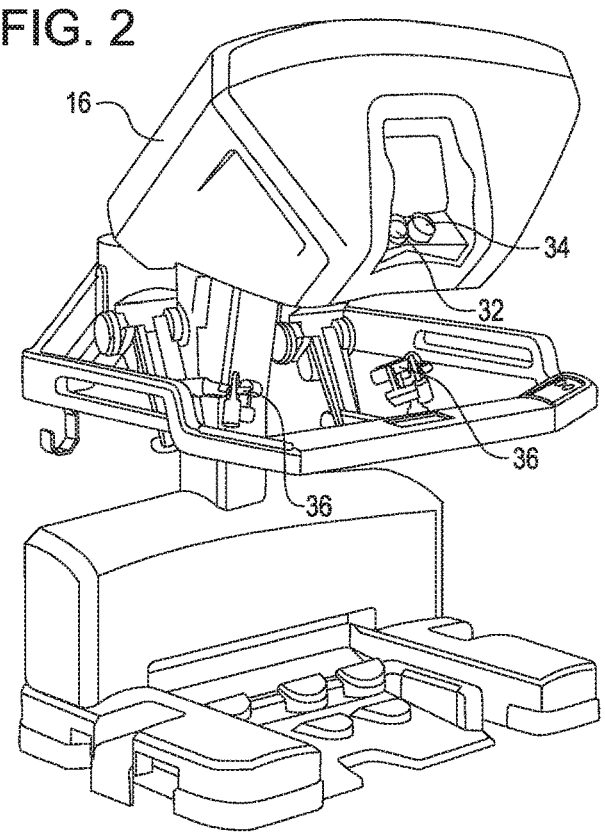
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
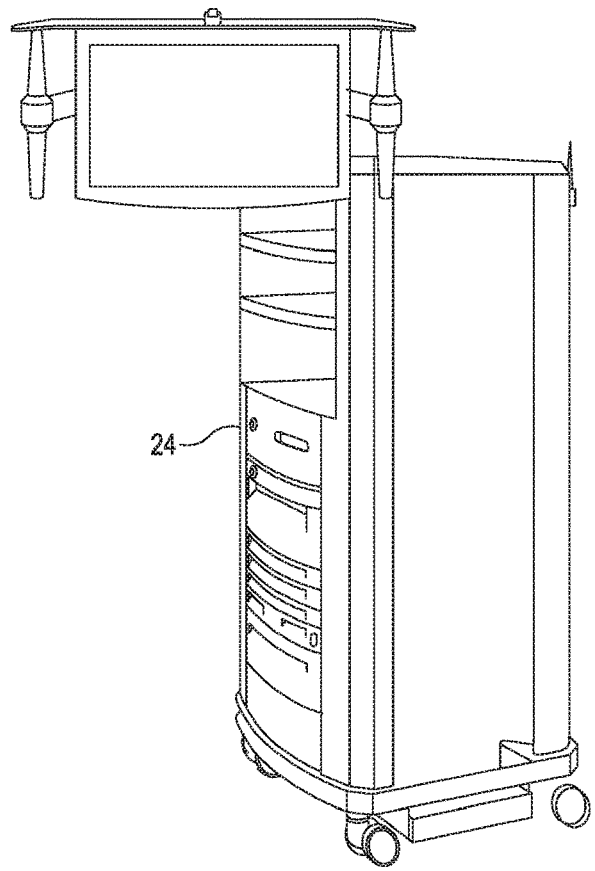
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
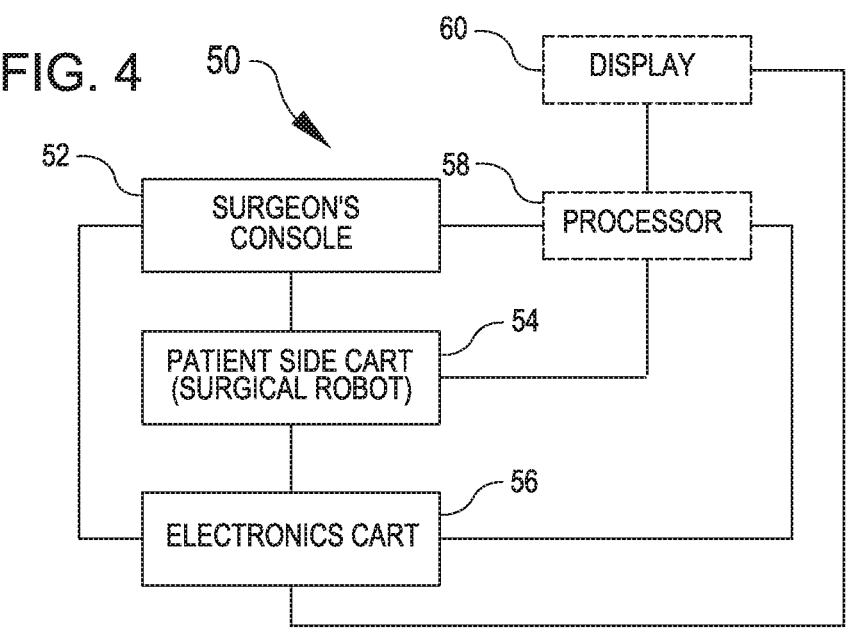
FIG. 4 diagrammatically illustrates a robotic surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5A:
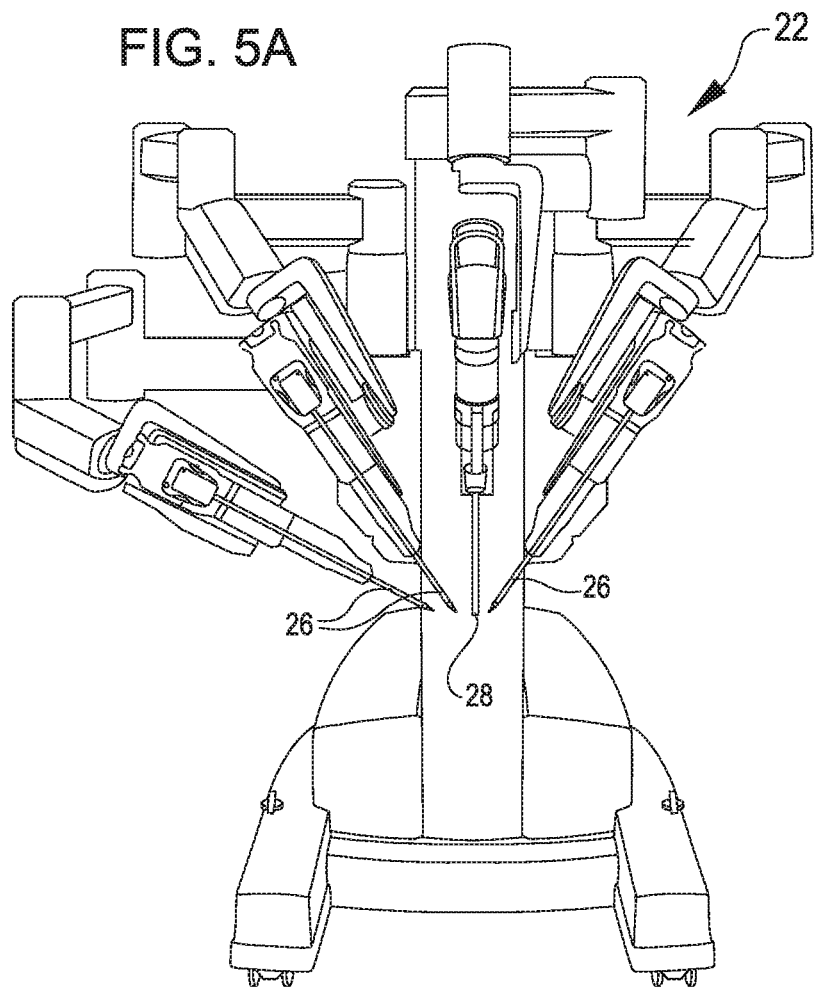
FIG. 5A is a front view of a patient side cart (surgical robot) of a robotic surgery system, in accordance with many embodiments.
Figure 5B:
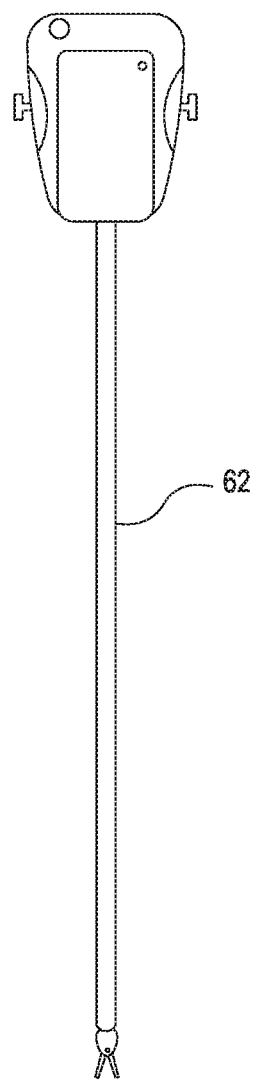
FIG. 5B is a front view of a robotic surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

FIG. 6 shows a surgical tool 70 that includes a proximal chassis 72, an instrument shaft 74, and a distal end effector 76 having a jaw 78 that can be articulated to grip a patient tissue. The proximal chassis includes input couplers that are configured to interface with and be driven by corresponding output couplers of the Patient Side Cart 22. The input couplers are drivingly coupled with drive shafts that are disposed within the instrument shaft 74. The drive shafts are drivingly coupled with the end effector 76.

Automated Assessment of Stapler Cartridge Status

FIG. 7 is a cross-sectional side view of an end effector 76 of a surgical instrument with a mounted stapler cartridge 84, in accordance with many embodiments. The stapler cartridge 84 is replaceable, for example, by demounting a used stapler cartridge from the end effector 76 and mounting a new stapler cartridge to the end effector 76. The end effector 76 includes an articulable anvil jaw 86 that is configured to form free ends of staples deployed from the stapler cartridge 84 and penetrated through tissue clamped between the stapler cartridge 84 and the anvil jaw 86. The stapler cartridge 84 includes a stapler cartridge body 88 that houses staples and a staple pushing shuttle 90 that is articulated distally along the stapler cartridge body 88 to push staples out of the stapler cartridge body 88 to penetrate through and staple tissue clamped between the stapler cartridge body 88 and the anvil jaw 86. The staple pushing shuttle 90 has a ramped portion 92 that interfaces with ramped staple pushers 94 (shown in FIG. 9 and FIG. 10) to push the staple pushers and the staples transversely out of the stapler cartridge body 88 relative to the motion of the staple pushing shuttle 90. The end effector 76 includes a pusher member 96 that is operatively coupled with an actuation mechanism via a push rod 98. An initial distal articulation of the pusher member 96 can be used to move the pusher member 96 into contact with the staple pushing shuttle 90. Further distal articulation of the pusher member 96 can be used to push the staple pushing shuttle 90 distally along the stapler cartridge body 88 and thereby force staples out of the stapler cartridge body 88. The pusher member 96 can be moved between a proximal limit position in which the pusher member 96 contacts a portion of the end effector other than the staple pushing shuttle 90 and a position in which the pusher member 96 contacts the staple pushing shuttle 90. As described herein, the distance between the proximal limit position and the position in which the pusher member 96 initially contacts the staple pushing shuttle 90 can be varied depending on the length of staples in the mounted stapler cartridge 84 and can be used to detect what type of stapler cartridge 84 is mounted to the end effector 76.

FIG. 8 is a top view of an embodiment of the stapler cartridge body 88. The staple cartridge body 88 has an array of staple accommodating apertures 100 in which staples and associated staple pushers are housed and from which the staples are deployed via articulation of the staple pushing shuttle 90 distally along the stapler cartridge body 88. The staple cartridge body 88 also has a central guide channel 102 and side guide channels 104 that accommodate and guide complementary shaped features of the staple pushing shuttle 90 during articulation of the staple pushing shuttle 90 distally along the stapler cartridge body 88. The central guide channel 102 also accommodates the pusher member 96 during articulation of the pusher member 96 distally along the staple cartridge body 88.

Figure 9:
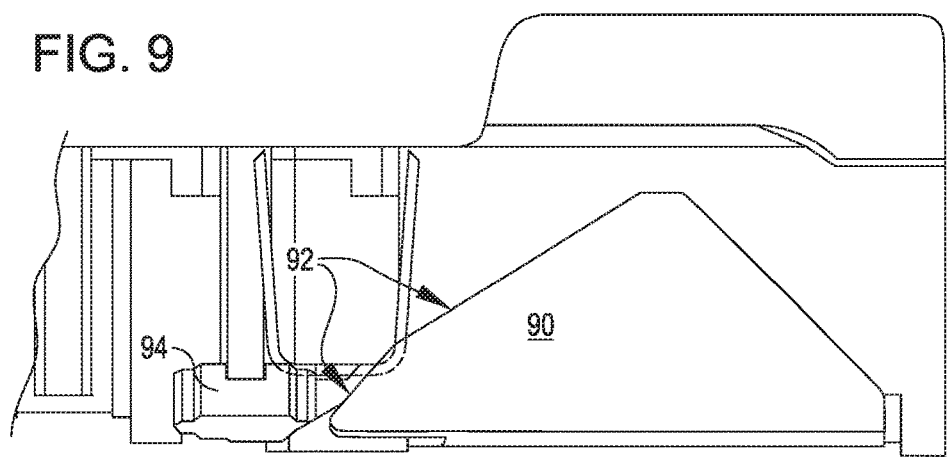
FIG. 9 is a partial cross-sectional side view of a stapler cartridge having relatively long staples, in accordance with many embodiments.
Figure 10:
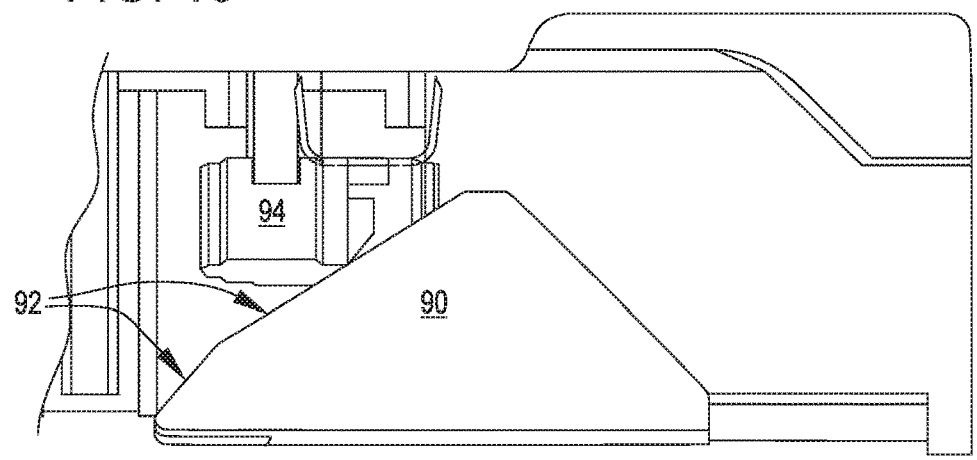
FIG. 10 is a partial cross-sectional side view of a stapler cartridge having relatively short staples, in accordance with many embodiments.

In many embodiments, the initial position of the staple pushing shuttle 90 along the stapler cartridge body 88 is varied and used to identify the type of the mounted stapler cartridge (e.g., the staple length of the mounted stapler cartridge). Specifically, for shorter staples, the staple pushing shuttle 90 can be disposed more distally along the stapler cartridge body 88 as compared to longer staples because the staple pushers for the shorter staples do not interact with a distal portion of the ramped portion 92 of the staple pushing shuttle 90. For example, as illustrated in FIG. 9, the initial position of staple pushing shuttle 90 must be proximal enough to permit the distal portion of the ramped portion 92 to interact with proximal-most staple pusher 94 for the longest staples. In comparison, as illustrated in FIG. 10, the initial position of the staple pushing shuttle 90 can be more distal for a shorter staple as compared to the longer staple shown in FIG. 9 because the staple pusher 94 can be disposed closer to the top of the stapler cartridge body 88 thereby accommodating a distal portion of the staple pushing shuttle 90 underneath the proximal-most staple pusher 94.

Figure 11:
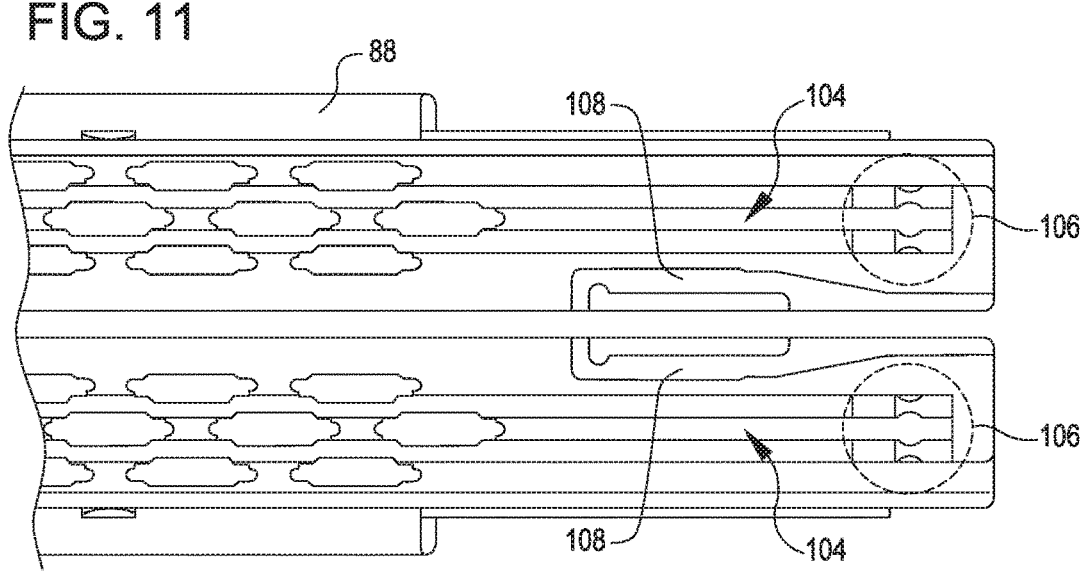
FIG. 11 is a top view of the proximal portion of the body of the stapler cartridge of FIG. 7 illustrating detent features that interface with a staple pushing shuttle to control starting location of the staple pushing shuttle, in accordance with many embodiments.

FIG. 11 is a top view of the proximal portion of an embodiment of the stapler cartridge body 88. The side guide channels 104 have detent features 106 that interface with complementary shaped detent features of the staple pushing shuttle 90 to control the initial position of the staple pushing shuttle 90 along the stapler cartridge body 88. In many embodiments, the detent features 106 are used to position the staple pushing shuttle 90 at a respective known position along the stapler cartridge body 88 for each type of stapler cartridge 84, wherein each type of stapler cartridge 84 has a respective staple length. The stapler cartridge body 88 also has a reuse-blocking spring clip mounting area 108 that is shaped to accommodate and support reuse-blocking spring clips 110 (shown in FIG. 12 through FIG. 17).

FIG. 12 through FIG. 16 illustrate respective nominal positional relationships between the pusher member 96 (positioned proximally into contact with a portion of the end effector 76) and the staple pushing shuttle 90 for five different types of stapler cartridges having five different respective staple lengths. In many embodiments, the pusher member 96 is articulated to measure the initial distance between the pusher member 96 and the staple pushing shuttle 90 and the measured initial distance is evaluated to determine the type of stapler cartridge that is mounted to the end effector 76. FIG. 12 through FIG. 16 also illustrate the reuse-blocking spring clips 110 in a pre-use configuration in which a portion of the staple pushing shuttle 90 is disposed between the reuse-blocking spring clips 110 to separate the reuse-blocking spring clips 110 to accommodate distal articulation of the pusher member 96 between the reuse-blocking spring clips 110 to push the staple pushing shuttle 90 distally to deploy staples.

Figure 12:
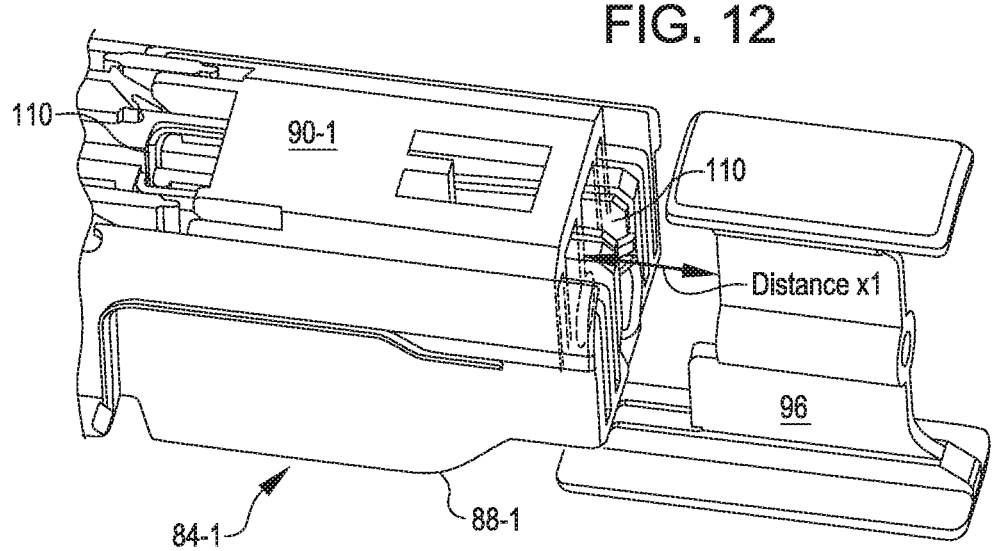
FIG. 12 illustrates a nominal positional relationship between a pusher member of an end effector and a staple pushing shuttle of a first type of stapler cartridge, in accordance with many embodiments.

FIG. 12 illustrates a first type of stapler cartridge 84-1 having the longest staple length. In FIG. 12, the staple pushing shuttle 90-1 is shown disposed at the initial position and secured relative to the stapler cartridge body 88-1 via engagement between the detent features 106 of the stapler cartridge body 88-1 and the interfacing complementary-shaped detent features of the staple pushing shuttle 90-1. In the first type of stapler cartridge 84-1, the pusher member 96 is disposed a first nominal distance (x1) from the staple pushing shuttle 90-1.

Figure 13:
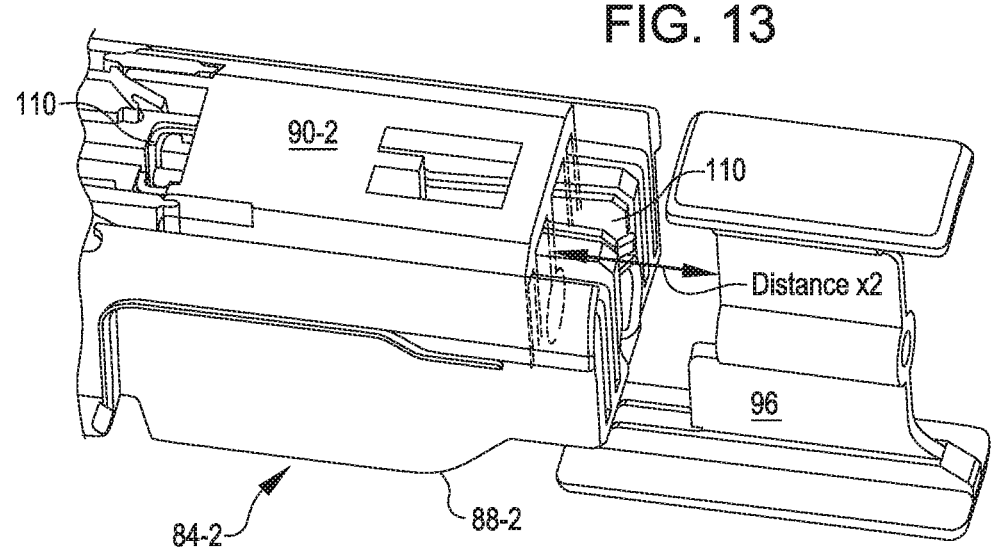
FIG. 13 illustrates a nominal positional relationship between a pusher member of an end effector and a staple pushing shuttle of a second type of stapler cartridge, in accordance with many embodiments.

FIG. 13 illustrates a second type of stapler cartridge 84-2 having a staple length shorter than the first type of stapler cartridge 84-1 shown in FIG. 12. In FIG. 13, the staple pushing shuttle 90-2 is shown disposed at the initial position and secured relative to the stapler cartridge body 88-2 via engagement between the detent features 106 of the stapler cartridge body 88-2 and the interfacing complementary-shaped detent features of the staple pushing shuttle 90-2. In the second type of stapler cartridge, the pusher member 96 is disposed a second nominal distance (x2) from the staple pushing shuttle 90-2. The second nominal distance (x2) is greater than the first nominal distance (x1) by a suitable distance so that the first and second types of stapler cartridges 84-1, 84-2 can be reliably differentiated based on the measured initial distance between the pusher member 96 and the staple pushing shuttle 90-2.

Figure 14:
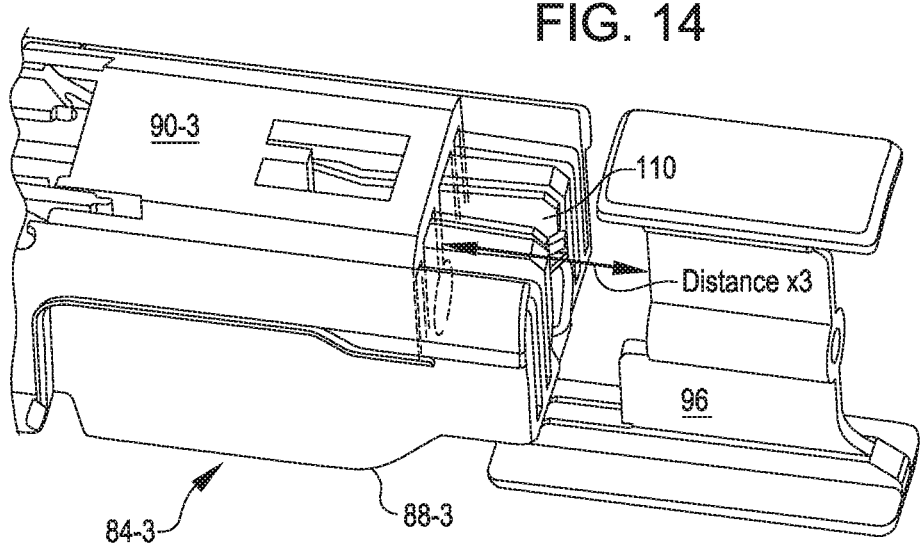
FIG. 14 illustrates a nominal positional relationship between a pusher member of an end effector and a staple pushing shuttle of a third type of stapler cartridge, in accordance with many embodiments.

FIG. 14 illustrates a third type of stapler cartridge 84-3 having a staple length shorter than the second type of stapler cartridge 84-2 shown in FIG. 13. In FIG. 14, the staple pushing shuttle 90-3 is shown disposed at the initial position and secured relative to the stapler cartridge body 88-3 via engagement between the detent features 106 of the stapler cartridge body 88-3 and the interfacing complementary-shaped detent features of the staple pushing shuttle 90-3. In the third type of stapler cartridge, the pusher member 96 is disposed a third nominal distance (x3) from the staple pushing shuttle 90-3. The third nominal distance (x3) is greater than the second nominal distance (x2) by a suitable distance so that the second and third types of stapler cartridges 84-2, 84-3 can be reliably differentiated based on the measured initial distance between the pusher member 96 and the staple pushing shuttle 90-3.

Figure 15:
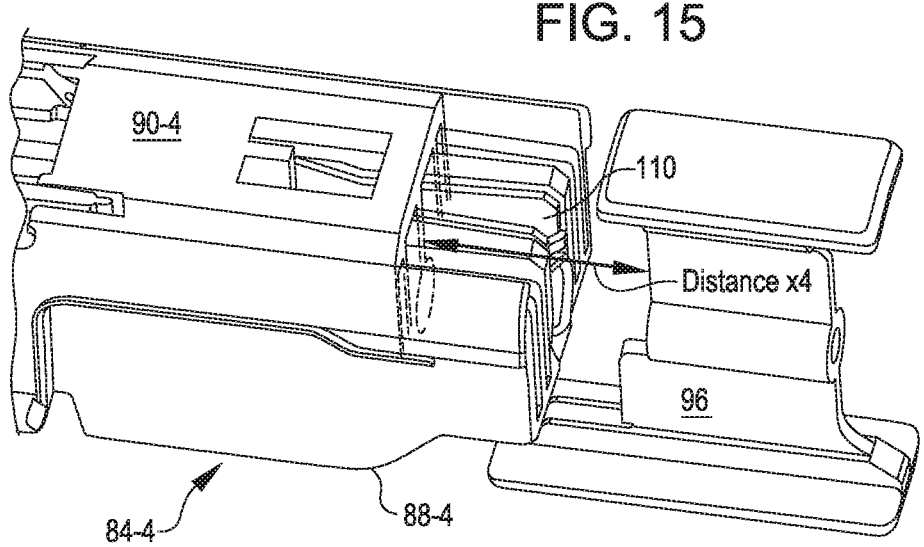
FIG. 15 illustrates a nominal positional relationship between a pusher member of an end effector and a staple pushing shuttle of a fourth type of stapler cartridge, in accordance with many embodiments.

FIG. 15 illustrates a fourth type of stapler cartridge 84-4 having a staple length shorter than the third type of stapler cartridge 84-3 shown in FIG. 14. In FIG. 15, the staple pushing shuttle 90-4 is shown disposed at the initial position and secured relative to the stapler cartridge body 88-4 via engagement between the detent features 106 of the stapler cartridge body 88-4 and the interfacing complementary-shaped detent features of the staple pushing shuttle 90-4. In the fourth type of stapler cartridge, the pusher member 96 is disposed a fourth nominal distance (x4) from the staple pushing shuttle 90-4. The fourth nominal distance (x4) is greater than the third nominal distance (x3) by a suitable distance so that the third and fourth types of stapler cartridges 84-3, 84-4 can be reliably differentiated based on the measured initial distance between the pusher member 96 and the staple pushing shuttle 90-4.

Figure 16:
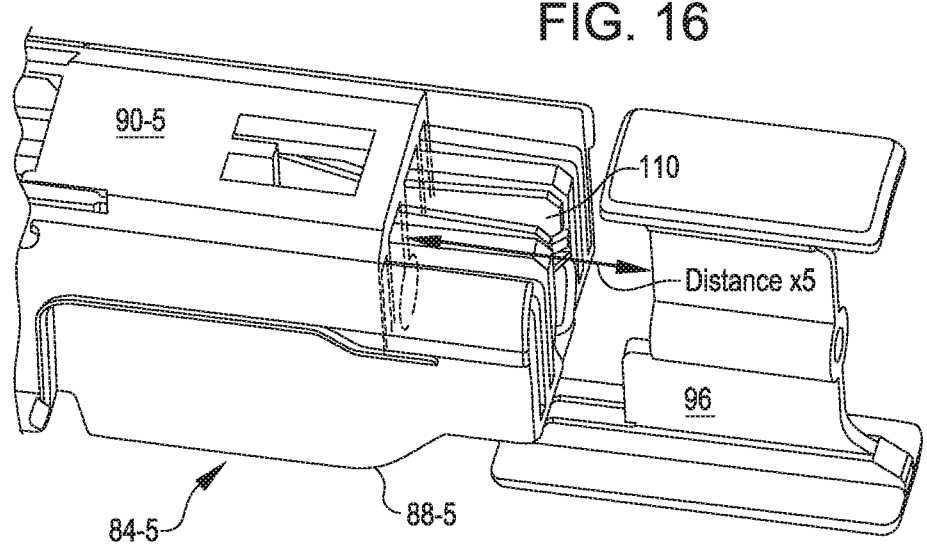
FIG. 16 illustrates a nominal positional relationship between a pusher member of an end effector and a staple pushing shuttle of a fifth type of stapler cartridge, in accordance with many embodiments.

FIG. 16 illustrates a fifth type of stapler cartridge 84-5 having a staple length shorter than the fourth type of stapler cartridge 84-4 shown in FIG. 15. In FIG. 16, the staple pushing shuttle 90-5 is shown disposed at the initial position and secured relative to the stapler cartridge body 88-5 via engagement between the detent features 106 of the stapler cartridge body 88-5 and the interfacing complementary-shaped detent features of the staple pushing shuttle 90-5. In the fifth type of stapler cartridge, the pusher member 96 is disposed a fifth nominal distance (x5) from the staple pushing shuttle 90-5. The fifth nominal distance (x5) is greater than the fourth nominal distance (x4) by a suitable distance so that the fourth and fifth types of stapler cartridges 84-4, 84-5 can be reliably differentiated based on the measured initial distance between the pusher member 96 and the staple pushing shuttle 90-5.

Figure 17:
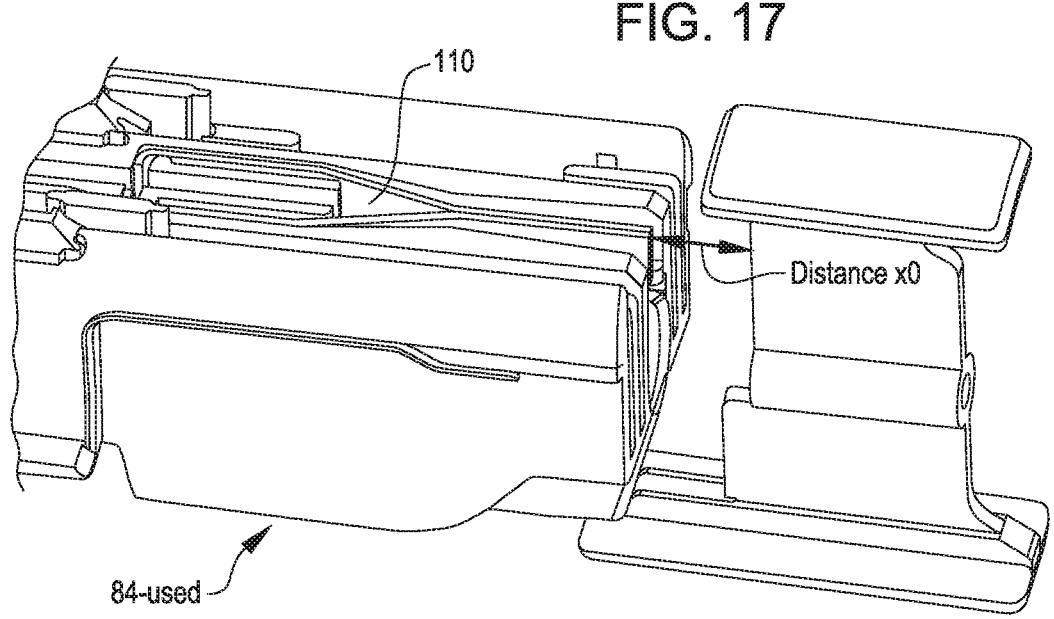
FIG. 17 illustrates a nominal positional relationship between a pusher member of an end effector and blocking spring clips of a stapler cartridge, in accordance with many embodiments.

FIG. 17 illustrates a nominal positional relationship between the pusher member 96 (positioned proximally into contact with a portion of the end effector 76) and the reuse-blocking spring clips 110 when a previously-used stapler cartridge (84—used) is mounted to the end effector 76. In FIG. 17, as a result of the prior use of the stapler cartridge (84—used), the staple pushing member 90 has already been articulated distally, thereby no longer holding the reuse-blocking spring clips 110 apart so that the reuse-blocking spring clips 110 have reconfigured from the pre-use configuration shown in each of FIG. 12 through FIG. 16 to the post-use configuration shown in FIG. 17. In the post-use configuration, the reuse-blocking spring clips 110 block distal articulation of the pusher member 96 past the reuse-blocking spring clips 110. When a previously-used stapler cartridge (84—used) is mounted to the end effector, the pusher member 96 is disposed a post-use nominal distance (x0) from the reuse-blocking spring clips 110 in the post-use configuration. The post-use nominal distance (x0) is less than the first nominal distance (x1) by a suitable distance so that a previously-used stapler cartridge (84—used) and the first type of stapler cartridge 84-1 can be reliably differentiated based on the measured initial distance between the pusher member 96 and either the staple pushing shuttle 90-1 or the reuse-blocking spring clips 110.

In many embodiments, the systems, devices, and methods described herein include detecting when no stapler cartridge is mounted to the end effector. When no stapler cartridge is mounted to the end effector, the initial distal articulation of the pusher member 96 (from being positioned proximally into contact with a portion of the end effector 76) occurs without the pusher member 96 coming into contact with either the reuse-blocking spring clips 110 or the staple pushing shuttle 90 due to lack of a mounted stapler cartridge. Accordingly, when the pusher member 96 has been articulated equal to or greater than a missing cartridge distance (xm), a determination can be made that no stapler cartridge is mounted to the end effector 76. The missing cartridge distance (xm) can be greater than the fifth nominal distance (x5) by a suitable distance so that a missing stapler cartridge and the fifth type of stapler cartridge 84-5 can be reliably differentiated.

FIG. 18 is a simplified block diagram of acts of a method 200 of assessing operational status of a surgical instrument for stapling tissue, in accordance with many embodiments. While the method 200 is described herein with respect to the surgical systems and surgical devices described herein, any suitable surgical system or surgical device can be used to practice the method 200.

In act 200, an actuation mechanism is operated to position the pusher member 96 at a known first position. Any suitable known first position can be used. For example, in many embodiments, the actuation mechanism is operated to retract the pusher member 96 proximally into contact with a portion of the end effector 76 to which the stapler cartridge 84 is mounted. The actuation mechanism can then be operated to articulate the pusher member 96 distally from the known first position to measure a distance from the known first position to the staple pushing shuttle 90 or the reuse-blocking spring clips 110 for use in assessing the operational status of the surgical instrument. As another example, the actuation mechanism can be operated to articulate the pusher member 96 distally into contact with either the staple pushing shuttle 90 or the reuse-blocking spring clips 110. The actuation mechanism can then be operated to retract the pusher member 96 proximally to measure a distance from the known first position to a position in which the pusher member 96 contacts a portion of the end effector 76 for use in assessing the operational status of the surgical instrument based on the distance through which the pusher member 96 is articulated. The known first position can also be at any suitable known distance from either a portion of the end effector 76, the staple pushing shuttle 90, or the reuse-blocking spring clips 110.

In act 204, operation of the actuation mechanism is limited to prevent unintended displacement of the staple pushing shuttle 90. For example, in many embodiments, the actuation mechanism is operated so as to be capable of only applying limited force to the pusher member 96 via the actuation rod 98 so that the pusher member 96 cannot apply sufficient force to the staple pushing shuttle 90 to cause disengagement of the staple pushing shuttle 90 from the detent features 106 of the stapler cartridge body 88.

In act 206, the actuation mechanism is operated to move the pusher member 96 from the first position to a second position from which further movement of the pusher member 96 away from the first position is inhibited due to contact with a stapler cartridge 84 mounted to the surgical instrument or a portion of the surgical instrument offset from the stapler cartridge 84. In many embodiments, the actuation mechanism is monitored to determine an operational parameter of the actuation mechanism indicative of the amount of movement of the pusher member 96 from the first position to the second position.

In act 208, an attribute of the stapler cartridge 84 is selected based on the amount of movement of the pusher member 96 from the first position to the second position. For example, the attribute of the stapler cartridge 84 can be selected based on the operational parameter of the actuation mechanism indicative of the amount of movement of the pusher member 96 from the first position to the second position. The selected attribute of the stapler cartridge 84 can be the type of stapler cartridge (e.g., staple length of the cartridge), whether the stapler cartridge has already been used, or whether no stapler cartridge is mounted to the end effector.

Other variations are within the spirit of the present invention. For example, while five different types of stapler cartridges are described herein, any suitable number of stapler cartridge types can be employed including fewer and more than the described five stapler cartridge types. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of assessing operational status of a surgical instrument for stapling tissue via a replaceable stapler cartridge, the method comprising:
   operating, under control of a control unit, an actuation mechanism drivingly coupled with a pusher member to attempt to move the pusher member from a first position to a second position subject to a force limit for the actuation mechanism;
   determining whether the actuation mechanism exceeded the force limit during the attempt to move the pusher member from the first position to the second position; and
   in response to determining that the actuation mechanism exceeded the force limit:
      determining, by the control unit, a distance of movement of the pusher member from the first position to a third position during the attempt to move the pusher member from the first position to the second position; and
      determining, by the control unit based on the distance of movement, an operational status of the surgical instrument relating to the replaceable stapler cartridge.

2. The method of claim 1, wherein:
   the pusher member reaches the second position during the attempt to move the pusher member from the first position to the second position; and determining the operational status of the surgical instrument relating to the replaceable stapler cartridge based on the distance of movement comprises determining that no replaceable stapler cartridge is mounted to the surgical instrument.

3. The method of claim 1, wherein:
the pusher member stops moving at a stop position due to an exceedance of the force limit for the actuation mechanism during the attempt to move the pusher member from the first position to the second position; and
determining the operational status of the surgical instrument relating to the replaceable stapler cartridge based on the distance of movement comprises determining that the replaceable stapler cartridge is mounted to the surgical instrument.

4. The method of claim 3, wherein:
the stop position is located within an initial range of motion between the first position and the second position; and
determining the operational status of the surgical instrument relating to the replaceable stapler cartridge based on the distance of movement comprises determining that the replaceable stapler cartridge mounted to the surgical instrument has already been fired.

5. The method of claim 3, wherein:
the stop position is located outside an initial range of motion between the first position and the second position; and
determining the operational status of the surgical instrument relating to the replaceable stapler cartridge based on the distance of movement comprises determining that the replaceable stapler cartridge mounted to the surgical instrument has not been fired.

6. The method of claim 5, wherein determining the operational status of the surgical instrument relating to the replaceable stapler cartridge based on the distance of movement comprises determining a type of the replaceable stapler cartridge mounted to the surgical instrument from a plurality of types of the replaceable stapler cartridge.

7. The method of claim 6, further comprising operating the actuation mechanism to move the pusher member to a fourth position further away from the first position than the second position subject to a second force limit for the actuation mechanism greater than the force limit for the actuation mechanism, wherein movement of the pusher member is discontinued if the second force limit for the actuation mechanism is exceeded during the attempt to move the pusher member to the second position.

8. The method of claim 1, further comprising operating the actuation mechanism, under the control of the control unit, to position the pusher member at the first position prior to the attempt to move the pusher member from the first position to the second position.

9. The method of claim 8, wherein operating the actuation mechanism to position the pusher member at the first position prior to the attempt to move the pusher member from the first position to the second position comprises moving the pusher member away from the second position into contact with a portion of the surgical instrument that blocks further movement of the pusher member away from the second position.

10. The method of claim 1, further comprising constraining a staple pushing shuttle of the replaceable stapler cartridge with a body of the replaceable stapler cartridge to at least one of:
position the staple pushing shuttle relative to the body of the replaceable stapler cartridge; or
inhibit displacement of the staple pushing shuttle relative to the body of the replaceable stapler cartridge when the replaceable stapler cartridge is contacted by the pushing member during the attempt to move the pusher member from the first position to the second position.

11. A surgical system configurable to staple tissue via a replaceable stapler cartridge, the surgical system comprising:
a surgical instrument including:
an end effector configured for mounting of a replaceable stapler cartridge to the end effector;
a pusher member configured to push a staple pushing shuttle included in the replaceable stapler cartridge to deploy staples from the replaceable stapler cartridge;
an elongated shaft to which the end effector is mounted at a distal end of the elongated shaft; and
a proximal chassis supporting a proximal end of the elongated shaft and including an actuation input drivingly coupled with the pusher member;
a manipulator to which the proximal chassis can be mounted, the manipulator including an actuation output configured to be drivingly coupled with the actuation input;
an actuation mechanism drivingly coupled with the actuation output; and
a control unit configured to:
control operation of the actuation mechanism to articulate the actuation output so as to attempt to move the pusher member from a first position to a second position subject to a force limit for the actuation mechanism,
determine whether the actuation mechanism exceeded the force limit during the attempt to move the pusher member from the first position to the second position, and
in response to determining that the actuation mechanism exceeded the force limit:
determine a distance of movement of the pusher member from the first position to a third position during the attempt to move the pusher member from the first position to the second position, and
determine, based on the distance of movement, an operational status of the surgical instrument relating to the replaceable stapler cartridge.

12. The surgical system of claim 11, wherein the control unit is configured to determine that no stapler cartridge is mounted to the end effector in response to the pusher member reaching the second position during the attempt to move the pusher member from the first position to the second position.

13. The surgical system of claim 11, wherein the control unit is configured to determine that a stapler cartridge is mounted to the end effector in response to the pusher member stopping at a stop position due to an exceedance of the force limit for the actuation mechanism during the attempt to move the pusher member from the first position to the second position.

14. The surgical system of claim 13, wherein the control unit is configured to determine that the stapler cartridge mounted to the end effector has already been fired in response to the stop position being located within an initial range of motion between the first position and the second position.

15. The surgical system of claim 13, wherein the control unit is configured to determine that the stapler cartridge mounted to the end effector has not been fired in response to the stop position being located outside an initial range of motion between the first position and the second position.

16. The surgical system of claim 15, wherein the control unit is configured to determine, based on the distance of movement, a type of the replaceable stapler cartridge mounted to the surgical instrument from a plurality of types of the replaceable stapler cartridge.

17. The surgical system of claim 16, wherein the control unit is configured to operate the actuation mechanism to move the pusher member to a fourth position further away from the first position than the second position subject to a second force limit for the actuation mechanism greater than the force limit for the actuation mechanism, wherein movement of the pusher member is discontinued if the second force limit for the actuation mechanism is exceeded.

18. The surgical system of claim 11, wherein the control unit is configured to operate the actuation mechanism to position the pusher member at the first position prior to the attempt to move the pusher member from the first position to the second position.

19. The surgical system of claim 18, wherein the control unit is configured to operate the actuation mechanism to move the pusher member away from the second position into contact with a portion of the end effector that blocks further movement of the pusher member away from the second position to position the pusher member at the first position.

20. The surgical system of claim 11, wherein the stapler cartridge comprises a body that constrains the staple pushing shuttle to at least one of:
   position the staple pushing shuttle relative to the body of the replaceable stapler cartridge; or
   inhibit displacement of the staple pushing shuttle relative to the body of the stapler cartridge when the stapler cartridge is contacted by the pushing member during the attempt to move the pusher member from the first position to the second position.

21. A surgical device configured to staple tissue via a stapler cartridge, the surgical device comprising:
   an end effector configured for mounting of a stapler cartridge to the end effector;
   a pusher member configured to articulate a staple pushing shuttle of the stapler cartridge to deploy staples from the stapler cartridge;
   an actuation mechanism drivingly coupled with the pusher member; and
   a control unit configured to:
      control operation of the actuation mechanism to attempt to move the pusher member from a first position to a second position subject to a force limit for the actuation mechanism;
      determine whether the actuation mechanism exceeded the force limit during the attempt to move the pusher member from the first position to the second position; and
      in response to determining that the actuation mechanism exceeded the force limit:
         determine a distance of movement of the pusher member from the first position to a third position during the attempt to move the pusher member from the first position to the second position; and
         based on the distance of movement of the pusher member achieved during the attempt to move the pusher member from the first position to the second position, determine:
            whether the stapler cartridge is mounted to the end effector; and
            if the stapler cartridge is mounted to the end effector, a type of the stapler cartridge selected from a plurality of possible types of the stapler cartridge or that the stapler cartridge has already been fired.

* * * * *